United States Patent [19]
Fulk et al.

[11] Patent Number: 5,814,023
[45] Date of Patent: Sep. 29, 1998

[54] ASPIRATOR SYRINGE OPERATOR

[75] Inventors: Paul F. Fulk, West Carrollton; Earnie S. Philpot, Centerville, both of Ohio

[73] Assignee: Para Tech Industries, Inc., Moraine, Ohio

[21] Appl. No.: 933,635

[22] Filed: Sep. 19, 1997

[51] Int. Cl.[6] .................................................. A61M 05/00
[52] U.S. Cl. ......................................... 604/232; 604/187
[58] Field of Search .................................. 604/187, 232, 604/181, 272; 606/1, 108, 183

[56] References Cited

U.S. PATENT DOCUMENTS

| | | | |
|---|---|---|---|
| 3,076,456 | 2/1963 | Mcconnaughey | 604/232 |
| 4,594,073 | 6/1986 | Stine | 604/232 |
| 4,643,724 | 2/1987 | Jobe | 604/232 |
| 5,368,578 | 11/1994 | Covington et al. | 604/232 |
| 5,395,379 | 3/1995 | Deutchman et al. | 606/123 |

*Primary Examiner*—Glenn K. Dawson
*Attorney, Agent, or Firm*—William Weigl, Esq.

[57] ABSTRACT

An aspirator syringe is provided with an operator mechanism which allows two fingers and the thumb of one hand to be used in a fist-closing direction to operate a syringe with good, steady, continuous-motion control, while permitting the other hand to be kept free to assure that the needle is kept intact in the patient. A simple mechanism for installing and removing a conventional syringe provides stability of the syringe and mechanism during aspiration and permits aspirated fluid to be dispensed either with or without removal of the syringe from the mechanism.

15 Claims, 2 Drawing Sheets

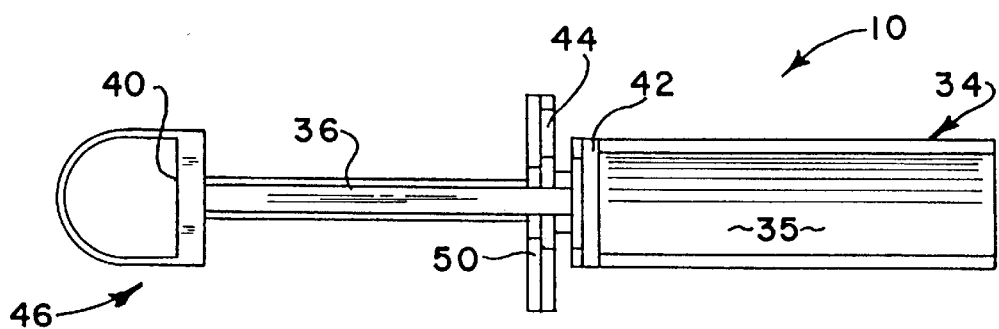
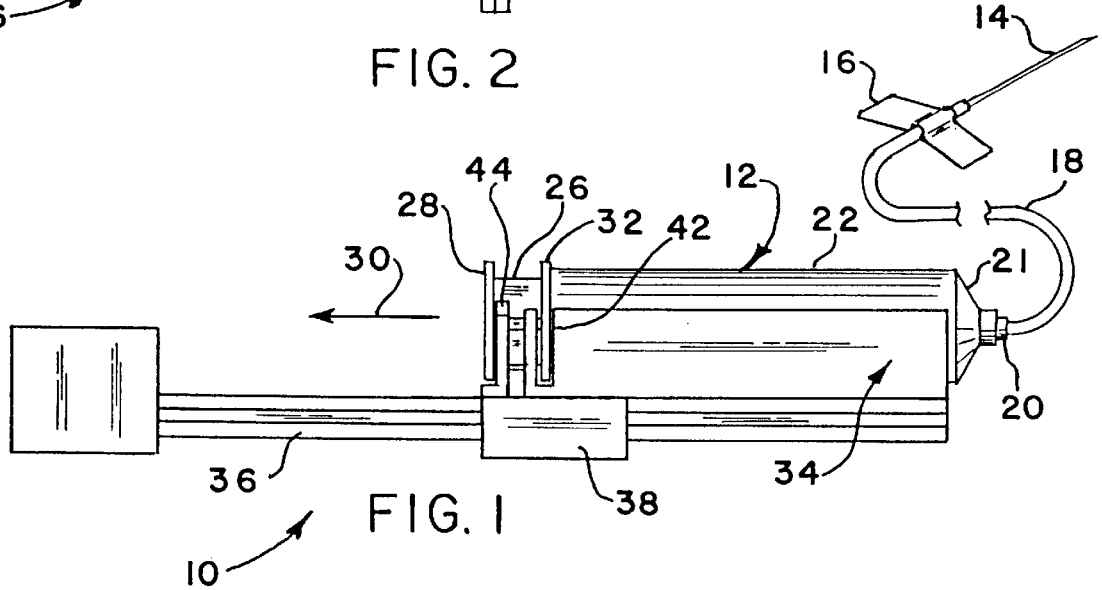
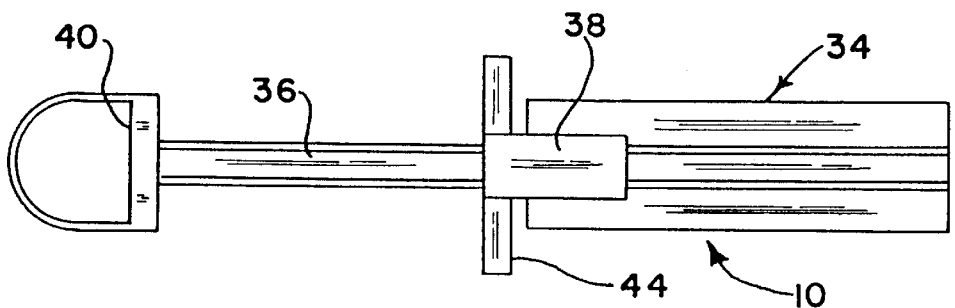

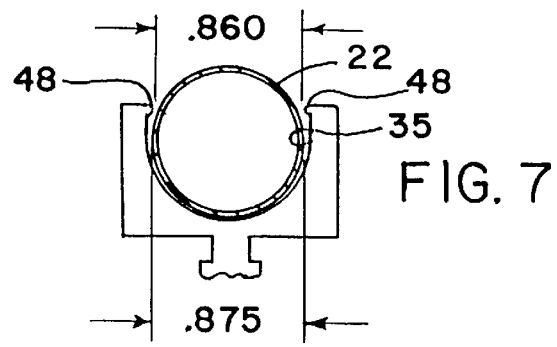
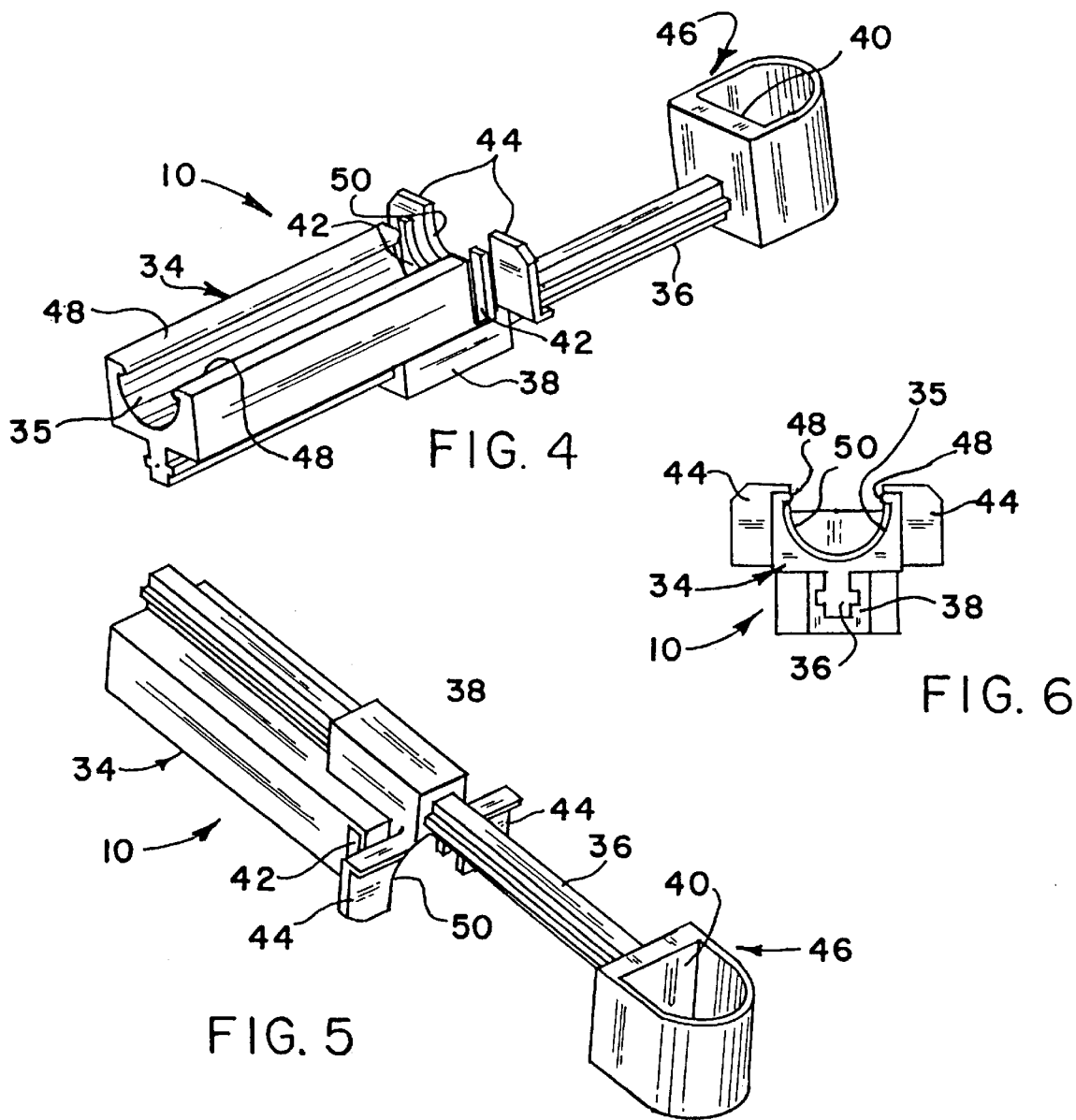

ASPIRATOR SYRINGE OPERATOR

This invention relates to an operator mechanism for a syringe of the type having a cylinder, a piston and a needle which are used to extract body fluid from a human or animal. In particular, it relates to a stable, relatively inexpensive, easily operable, disposable device which enables a single individual who is performing the extraction to manually collect fluid from a body while using only one hand to operate the syringe. The design is such that fluid can be dispensed from the syringe either while it remains in the device, or the syringe is easily removable for fluid dispensing independently of the device. This application is based on U.S. Provisional patent application Ser. No. 60/027,761 filed Oct. 7, 1996.

BACKGROUND

A typical syringe of the size used to withdraw a relatively large volume of blood includes a cylinder or barrel, a needle and tube extending therefrom, a piston having its periphery in sealing engagement with the inside diameter of the cylinder and gripping portions such as flanges at the end of the piston and cylinder remote from the needle end. When a needle is initially placed into a vein just below the skin, it is often taped in place to prevent premature or accidental withdrawal. The operator can then apply an outwardly-directed force between the cylinder and piston flanges to create a vacuum in the cylinder, allowing the cylinder to fill with blood in the volume desired. Since an airtight seal is present, considerable effort must sometimes be expended to move the piston outwardly of the cylinder. To avoid the possibility of accidental removal of the needle from the patient, it sometimes requires two persons to perform the extraction, one with both hands to operate the syringe, and another person to assure that the needle remains in place. Unless a helper is conveniently available, a single person generally performs the process with one hand to push against the piston flange with one finger while bracing the thumb and another finger against the cylinder flange to allow the pushing. The other hand is then free to hold the needle in place. This latter one-person operation approach is a bit difficult in many instances, with the extraction taking place in jerky finger-repositioning steps or stages rather than in one easy continuous motion, as is possible if the performer is given the capability of using both hands to operate the syringe.

Devices have been known in the patent art for mounting syringes in accessory devices to enable their operation while using but one hand to perform an aspiration. To the best of our knowledge, they have not found their way to the marketplace, but of this we cannot be certain. U.S. Pat. No. 3,819,091 issued to Hollender in 1974 discloses a pistol grip type system for positive injection or withdrawal operation. Only one hand moving in a fist-closing direction is necessary for fluid withdrawal. The pistol grip appears useless for positive injection, however, since it appears to require two hands, and the piston movement would be in the direction opposite to what would occur when using the pistol grip for withdrawal.

Another and much simpler design of a device for one-handed syringe aspiration is shown in U.S. Pat. No. 5,135,511 granted in 1992 to Houghton, et al. As depicted in the illustrated design, it appears incapable of use for dispensing fluid without first unclamping the main operating structure. It would require two hands to first accomplish the unclamping to enable the syringe to be removed for dispensing purposes. Once that is done, the syringe can be used as a standard injecting syringe with one hand. An alternative disclosed in the specification of Houghton '511 would allow two-handed dispensing with the syringe retained within the holder, but would require use of a non-conventional syringe with a special flange on the shaft end of the syringe piston.

SUMMARY OF THE INVENTION

An operating mechanism or device is provided for a conventional, off-the-shelf aspirating syringe. The device allows two fingers and the thumb of one hand to be used in a fist or hand-closing direction to operate a syringe with steady and continuous-motion control, while permitting the other hand to be kept free to assure that the needle is kept intact in the patient. The design of the device enables easy installation and removal of a syringe, and permits aspirated fluid to be dispensed with the syringe either removed from or remaining in the device. Especially during an aspirating operation, it is essential that the syringe be stably connected to the device. To achieve this end, provision is made for the syringe to be lightly pressed into position in the device and be firmly retained therein during aspiration. Upon completion of the aspirating function, the syringe may be easily snapped out of its retaining means, should it be desired to remove the syringe for dispensing of fluid into culture dishes or the like. Where used in connection with human beings, the device is ordinarily disposable along with the syringe, and dispensing can be done with the syringe remaining in the device if desired.

DESCRIPTION OF THE DRAWINGS

FIG. 1 is a side elevational view of a syringe holder and operator, illustrating one conventional type of aspirating syringe mounted in position for use therewith.

FIGS. 2 and 3 are top and bottom views respectively of the holder of FIG. 1, without the presence of a syringe.

FIG. 4 is an upper left side isometric view of the holder of FIGS. 1–3.

FIG. 5 is a lower isometric view of the holder.

FIG. 6 is an end view of the holder looking essentially in the direction of the arrow 6 of FIG. 4.

FIG. 7 is an enlarged schematic view similar to FIG. 6, illustrating the manner of capturing and retaining a syringe in the holder during an aspirating operation.

DESCRIPTION OF THE PREFERRED EMBODIMENT

FIGS. 1 through 3 are right side, top and bottom views respectively of that version of our invention in which an independent operating mechanism or holder 10 receives a conventional aspirator syringe 12. The syringe 12 is shown in FIG. 1 with a needle 14 connected to one end. The needle is typically provided with a thin "butterfly" 16, a thin flexible tube 18 and a threaded adaptor 20 with which the needle and tube are connected to the needle end 21 of the syringe 12. The syringe 12 comprises a barrel or cylinder 22, an internal piston (not shown), a shaft 26 connected to the piston and a flange 28 at the end of the shaft remote from the piston. The flange ordinarily serves to enable pulling of the shaft and piston away from the needle end 21 of the cylinder in conventional fashion during blood or other liquid extraction. The cylinder is typically made of transparent plastic and is provided with graduations (not shown) on its exterior to enable the person extracting a body fluid to see and withdraw the desired volume from the patient. The needle 14 is placed below the patient's skin and inserted into a vein. The butterfly 16 serves to anchor the needle in place by providing a surface to which adhesive tape can be applied so that the needle can be kept flat and secure against the patient while blood is being extracted.

Using the type of syringe shown, but without any holder of the type described herein or in the aforementioned patents, particularly if a large volume of blood such as twenty cc. is needed, two persons are often required to perform the extracting function. In an understaffed or busy hospital or clinic, an assistant is not always available. It can and frequently is done by a single person, but with some difficulty, with one hand operating the piston and the other protecting against accidental needle removal. At the start of aspiration by one individual, the piston is all the way rightwardly of a flange 32 so that the piston is directly against the needle end of the cylinder 22. It should be understood that the syringe is being described at this point as it is shown in FIG. 1, but without being in the holder, i.e., the syringe is being used by itself.

At the end of the cylinder 22 opposite the needle end 21, the cylinder is open. One's fingers and thumb are then placed in the small (about one-half inch) space between the flange 28 and the opposing flange 32 extending radially from the open end of the cylinder. Spreading the fingers and thumb with a prying motion commences piston movement in the direction outwardly of the cylinder. The fingers and thumb are ordinarily repositioned several times during extraction, resulting in an uneven, staged extraction. All of this depends, of course, on the finger strength of the person operating the syringe and the amount of force required to overcome the vacuum as determined by the seal of the piston against the inside of the cylinder. The piston is typically a very soft rubber or comparable material having several separate thin sealing walls contacting the cylinder internally.

If smooth, continuous operation of the syringe is desired, one person can operate a syringe with both hands and another can keep the taped butterfly 16 in place while steadying the patient. When done in this fashion, the operator can hold the cylinder 22 in one hand and pull out reasonably steadily with fingers gripping the flange 28. The problem with this is the necessity of frequently using two people to perform the extraction, while only one person can easily accomplish the extraction with ease and with a steady, continuous motion by employing the features of our invention, which we will now describe.

The isometric views of FIGS. 4 and 5 nicely show the structure of the holder 10. The holder comprises a elongated body portion or member 34 having a concave, essentially U-shaped recess 35 for receiving the cylinder 22, an elongated guide track 36, a carriage 38 freely movable along the track 36 and a thumb-receiving pressure pad 40. The body member 34 is slotted at opposite sides of the recess 35 at its end nearest the carriage 38 as at 42, enabling reception of the cylinder flange 32 into the slots to prevent axial displacement of the cylinder relative to the body portion 34 during operation. As shown in FIG. 1, some clearance is provided between the sides of the flange 32 and the slots 42 to permit easy installation and removal of the syringe relative to the holder. With the person performing the extraction placing his or her thumb into a thumb-receiving portion 46 and having his or her first and second fingers placed on ribbed sides of diametrically-opposed wings 44 of carriage 38, the fingers can be drawn toward the thumb in a fist-closing direction. It will be noted that when the flange 32 of the cylinder is within the slots 42, the flange 28 of the piston shaft 26 contacts only that side of the wings 44 opposite the ribbed sides. Clearance of approximately one-sixteenth of an inch is desired between the inner side of the flange 28 and the wings 44, also to simplify installation and removal of the syringe. By applying force between the thumb pressure pad 40 and the wings 44 of the carriage 38 in a direction toward each other, the piston can be easily, steadily and continuously moved in the direction of the arrow 30 of FIG. 1 to the extent necessary to draw the amount of blood intended. Extraction is practically done as easily as later dispensing blood from the syringe, and is done with the normal dispensing-type motion. In effect, through use of our invention, the same type of fist-closing motion can be applied whether extracting or dispensing a fluid, whereas conventionally, different motions are required for each. Using a standard syringe and the holder 10, piston movement is discontinued when the end of the column of blood in the cylinder aligns with the appropriate graduation on the cylinder.

An important improvement of our holder design is to provide stability of the syringe 12 in the holder 10 during aspiration. To achieve this end, all parts are preferably produced from any one of several sterilizable medical-grade plastics which is also sufficiently flexible to enable the syringe to be pressed or snapped into and from the U-shaped recess 35. FIG. 7 illustrates one manner in which that stability can be achieved. In the example shown, the cylinder barrel has an outside diameter of 0.875 inches. The recess is larger in diameter, perhaps 0.9375 inches, or one-sixteenth of an inch greater in diameter than that of cylinder 22. The "U" shape of the recess may be obtained in several ways. As simply shown in FIG. 7, about 225 degrees of the circular recess 35 is plastic material and about 135 degrees is open. This provides for thin, inwardly-directed flexible edges, lips or beads 48 of lesser spacing (0.860 in the example shown) than the diameter of the cylinder 22. Thus, when installing the syringe 12 in the holder 10, it is moved laterally toward the body member 34, or downwardly in the direction of arrow 50 as shown in FIG. 1. At this time, wings 44 are in the position nearest the body member 34 and the carriage is underslung or overlapping relative to the body member. The flange 32 easily enters slots 42 and the flange 38 enters with ease leftwardly of wings 44. The cylinder 22 spreads the flexible beads 48 apart and passes into the recess 35 in a snapping action. The beads 48 also prevent lifting of the cylinder past the beads until they are again spread over center.

The carriage 38 and its guide track 36 may be of any desired well-known shape which maintains the carriage 38 against axial rotation as it moves along track 36. The length of the carriage stabilizes it longitudinally, but necessarily requires that it overlap the body member 34 in order to position the wings 44 closely enough to the syringe 12 to receive the flange 28.

Since the guide track 36 is offset laterally from the axis of the cylinder 22 in order to use a single guiding element, there is a natural tendency to introduce a mechanical couple between the wing 44 and the syringe 12, imparting a lifting motion of the syringe from the recess 35. This is opposed by the beads 48 which retain the syringe barrel in the recess as the shaft 26 is moved outwardly of the syringe.

After aspiration has been completed and the needle removed from the patient, the fluid can be dispensed in either of two ways. Since the carriage 38 and its wings 44 are freely movable along track 36, they can be permitted to float by gravity back to their starting position prior to aspiration. Then, using one hand to grip the body member 34 and syringe 12, and the thumb of the other hand to press the flange 28 back toward the cylinder, fluid can be dispensed from the needle into one or more containers, as is customary. Or, if it is desired to remove the syringe 12 from the holder 10 prior to dispensing the fluid, the syringe may be simply and easily unsnapped past the beads 48 in a direction opposite to arrow 50 of FIG. 1.

Obviously, the beads 48 may be continuous or intermittent along the length of the body member 34. Also, recess 35 can be a true U with a semi-cylindrical bottom and straight side wall portions extending upwardly from the semi-cylindrical bottom, or can be a cylindrical recess with the portions of the recess 35 above its center being considered wall portions and the edges adjacent the opening forming the beads 48.

In order to install the syringe in the holder, clearance for the shaft 26 through the wings 44 is provided by a second U-shaped recess 50 which is coaxially aligned with recess 35.

Various changes may be made without departing from the scope and spirit of the claims.

Having described our invention, we claim:

1. A device for operating an aspirating syringe having an elongated tubular cylinder with an open end and a needle end remote from the open end, a piston closing said open end and movable between said needle end and said open end for extracting body fluid through a hollow needle associated with the needle end and for dispensing the fluid through the needle when moved from said open end toward the needle end, said piston having a shaft extending outwardly therefrom beyond the open end of said cylinder and including a laterally outwardly-directed first flange at the shaft distal end, and a laterally outwardly-directed second flange integral with the cylinder and essentially surrounding its open end, said device comprising:

an elongated body member having a generally U-shaped recess extending the length thereof for nesting said cylinder therein during aspirating operation of said syringe, the cross-sectional shape of said recess comprising a semi-cylindrical portion and a wall portion at each side of said semi-cylindrical portion, said wall portions being spaced apart slightly in excess of said cylinder diameter;

an inwardly-directed flexible bead extending along each wall portion remote from said semi-cylindrical recess, said beads being spaced apart across said recess less than said cylinder diameter whereby said cylinder can be pressed laterally into said recess by spreading said beads and retained in said recess by said beads when in said recess;

a transverse slot adjacent an open end of the body member for laterally receiving said second flange when said cylinder is placed in said recess whereby to retain said cylinder against axial movement;

an elongated guide track affixed to said body member and extending away from the cylinder open end to a limit position of movement of said shaft;

a thumb pressure pad at an end of said track; and a carriage movable along said track, said carriage having outwardly-directed, diametrically-opposed wing portions enabling one hand operation of said carriage from a first position adjacent said cylinder open end in a thumb-and-two-finger closing operation toward a second position adjacent said thumb pressure pad, and said wing portions, when said syringe is pressed into said recess with said piston at the needle end of said cylinder, positioning said first flange intermediate said wing portions and said pressure pad to ready the syringe for operating said shaft and piston in an aspirating direction.

2. The device of claim 1 wherein said guide track extends parallel to and alongside at least a portion of said body member on a side thereof opposite said recess, and wherein said carriage has an elongated body portion which longitudinally overlaps said syringe when said wing portions are in position adjacent the open end of the cylinder to receive said first flange.

3. The device of claim 1 wherein said thumb pressure pad is provided with a thumb-encircling guard portion to prevent slippage of the operator's thumb from said pad during aspiration.

4. The device of claim 1 wherein said track has a cross-sectional shape throughout its length which steadies the carriage against rotational movement relative to said track during aspiration.

5. The device of claim 1 wherein said carriage wing portions are provided with a shaft-receiving recess therebetween, which recess is coaxial with said elongated body member recess and open on the same lateral side of said device whereby to enable lateral installation and removal of a syringe from the device.

6. The device of claim 1 wherein said wing portions are adapted to contact solely that side of said first flange nearest said cylinder, said carriage thereby being free to be slid toward said cylinder and away from said wing portions when the cylinder is filled with fluid, whereby to enable grasping of said shaft for lateral lifting of said syringe from said device for subsequent dispensing of fluid.

7. The device of claim 5 wherein said carriage is freely slidably mounted on said track toward and away from the body member, whereby the end of said piston shaft may be pressed toward said cylinder to dispense fluid while said syringe remains in said device.

8. The device of claim 1 wherein said body member, track, carriage and pressure pad are all produced from a sterilizable medical grade plastic.

9. A device for operating an aspirating syringe having an elongated tubular cylinder with an open end and a needle end remote from the open end, a piston closing said open end and movable between said needle end and said open end for extracting body fluid through a hollow needle associated with the needle end and for dispensing the fluid through the needle when moved from said open end toward the needle end, said piston having a shaft extending outwardly therefrom beyond the open end of said cylinder and including a laterally outwardly-directed first flange at the shaft distal end, and a laterally outwardly-directed second flange integral with the cylinder and essentially surrounding its open end, said device comprising:

an elongated body member having a generally U-shaped recess extending the length thereof for nesting said cylinder therein during aspirating operation of said syringe;

a transverse slot adjacent an open end of the body member for laterally receiving said second flange when said cylinder is placed in said recess whereby to retain said cylinder against axial movement;

an elongated guide track laterally affixed to and overlapping said body member on the side thereof opposite said recess, said track extending away from the cylinder open end to a limit position of movement of said shaft;

a thumb pressure pad at the end of said track remote from said cylinder;

a carriage movable along said track, said carriage having an elongated bearing portion providing sliding surface contact with said track and said carriage further having outwardly-directed, diametrically-opposed wing portions for straddling said shaft and enabling one hand operation of said carriage from a first position adjacent said cylinder open end in a thumb-and-two-finger closing operation toward a second position adjacent said thumb pressure pad; and said carriage bearing portion extending beneath said body member when in said first position and locating said wing portions to position said first flange intermediate said wing portions and said pressure pad to ready the syringe for operating said shaft and piston in an aspirating direction.

10. The device of claim 9 wherein said thumb pressure pad is provided with a thumb-encircling guard portion to prevent slippage of the operator's thumb from said pad during aspiration and wherein an opening is provided through said guard portion for passage therethrough of a person's thumb.

11. The device of claim 9 wherein said track has a cross-sectional shape throughout its length which steadies the carriage against rotational movement relative to said track during aspiration.

12. The device of claim 9 wherein said carriage wing portions are provided with a shaft-receiving recess therebetween, which recess is coaxial with said elongated body member recess and open on the same lateral side of said device whereby to enable lateral installation and removal of a syringe from the device.

13. The device of claim 9 wherein said wing portions are adapted to contact solely that side of said first flange nearest said cylinder, said carriage thereby being free to be slid toward said cylinder and away from said wing portions when the cylinder is filled with fluid, whereby to enable grasping of said shaft for lateral lifting of said syringe from said device for subsequent dispensing of fluid.

14. The device of claim 13 wherein said carriage is freely slidably mounted on said track toward and away from the body member, whereby the end of said piston shaft may be pressed toward said cylinder to dispense fluid while said syringe remains in said device.

15. The device of claim 9 wherein said body member, track, carriage and pressure pad are all produced from a sterilizable medical grade plastic.

* * * * *